United States Patent
Hong et al.

(10) Patent No.: US 11,255,932 B2
(45) Date of Patent: Feb. 22, 2022

(54) MAGNETIC-FIELD-GENERATING COIL SYSTEM, IMAGING SYSTEM HAVING MAGNETIC-FIELD-GENERATING COIL SYSTEM, AND METHOD FOR OPERATING IMAGING SYSTEM

(71) Applicant: ELECTRONICS AND TELECOMMUNICATIONS RESEARCH INSTITUTE, Daejeon (KR)

(72) Inventors: Hyo-Bong Hong, Daejeon (KR); Jae-Chan Jeong, Daejeon (KR); Seung-Min Choi, Daejeon (KR); Jin-Sun Kim, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 246 days.

(21) Appl. No.: 16/572,254

(22) Filed: Sep. 16, 2019

(65) Prior Publication Data
US 2020/0182952 A1 Jun. 11, 2020

(30) Foreign Application Priority Data

Dec. 10, 2018 (KR) .................. 10-2018-0158402
Apr. 2, 2019 (KR) .................. 10-2019-0038248

(51) Int. Cl.
*G01R 33/12* (2006.01)
*G01R 33/385* (2006.01)

(52) U.S. Cl.
CPC ....... *G01R 33/1276* (2013.01); *G01R 33/385* (2013.01)

(58) Field of Classification Search
CPC .. G01R 33/1276; G01R 33/385; G01R 33/48; A61B 5/7257; A61B 5/0515
See application file for complete search history.

(56) References Cited

U.S. PATENT DOCUMENTS

| | | | | |
|---|---|---|---|---|
| 4,509,011 A | * | 4/1985 | Sugimoto | G01R 33/4833 324/309 |
| 4,556,848 A | * | 12/1985 | Eberhard | G01R 33/54 324/307 |
| 8,188,744 B2 | | 5/2012 | Lee et al. | |

(Continued)

FOREIGN PATENT DOCUMENTS

| | | |
|---|---|---|
| JP | 2002291716 A | 10/2002 |
| KR | 1020180115170 A | 10/2018 |

OTHER PUBLICATIONS

Mason EE, Cooley CZ, Cauley SF, Griswold MA, Conolly SM, Wald LL. Design analysis of an MPI human functional brain scanner. Int J Magn Part Imaging, 2017 (Year: 2017).*

*Primary Examiner* — Daniel R Miller

(57) ABSTRACT

Disclosed herein are a magnetic-field-generating coil system, an imaging system having the magnetic-field-generating coil system, and a method for operating the imaging system. The method for operating an imaging system includes generating multiple Linear Gradient Fields (LGFs) in respective axial directions by controlling coil currents, and acquiring MRI information or Magnetic Particle Imaging (MPI) information about an object while moving the multiple LGFs by varying the coil currents.

18 Claims, 11 Drawing Sheets

(56) References Cited

U.S. PATENT DOCUMENTS

| | | | |
|---|---|---|---|
| 8,847,592 B2 * | 9/2014 | Goodwill | G01R 33/1269 |
| | | | 324/301 |
| 9,482,727 B2 | 11/2016 | Choi et al. | |
| 9,977,764 B2 | 5/2018 | Simola et al. | |
| 2003/0216636 A1 * | 11/2003 | Paley | G01R 33/445 |
| | | | 600/410 |
| 2006/0280689 A1 * | 12/2006 | Xiang | A61K 41/0052 |
| | | | 424/9.34 |
| 2007/0249926 A1 * | 10/2007 | McDougall | G01R 33/385 |
| | | | 600/410 |
| 2008/0309330 A1 * | 12/2008 | Oh | A61B 5/05 |
| | | | 324/232 |
| 2009/0115415 A1 * | 5/2009 | Weaver | A61B 5/0515 |
| | | | 324/309 |
| 2010/0127707 A1 | 5/2010 | Lee et al. | |
| 2012/0126808 A1 * | 5/2012 | Knopp | G01R 33/445 |
| | | | 324/301 |
| 2017/0003361 A1 | 1/2017 | Seeber et al. | |
| 2018/0292489 A1 | 10/2018 | Zeng et al. | |
| 2019/0213761 A1 * | 7/2019 | Rosen | A61B 5/0035 |

\* cited by examiner

MAGNETIC-FIELD-GENERATING COIL SYSTEM, IMAGING SYSTEM HAVING MAGNETIC-FIELD-GENERATING COIL SYSTEM, AND METHOD FOR OPERATING IMAGING SYSTEM

CROSS REFERENCE TO RELATED APPLICATIONS

This application claims the benefit of Korean Patent Application Nos. 10-2018-0158402, filed Dec. 10, 2018 and 10-2019-0038248, filed Apr. 2, 2019, which are hereby incorporated by reference in their entireties into this application.

BACKGROUND OF THE INVENTION

1. Technical Field

The present invention relates to a magnetic-field-generating coil system, an imaging system having the magnetic-field-generating coil system, and a method for operating the imaging system.

2. Description of the Related Art

Generally, noninvasive imaging equipment widely used in medical and industrial fields may be chiefly classified into imaging equipment using X-ray or X-ray Computed Tomography (CT), imaging equipment using ultrasonic waves, Positron Emission Tomography (PET) using radioactive substances, and imaging equipment based on electromagnetic fields. Among pieces of imaging equipment based on electromagnetic fields, the imaging equipment that is most widely used is a Magnetic Resonance Imaging (MRI) scanner. The most fundamental principle based on which the position at which resonance occurs is detected in all MRI scanners that have been developed to date is expressed by the Larmor equation, which is a proportional expression of the strength of a magnetic field produced in space and a Radio Frequency (RF). That is, the Larmor equation is represented by $W = g \times B$, where W=Larmor frequency, g=gyromagnetic ratio, and B=strength (Tesla) of an applied magnetic field.

In order to detect the position at which electromagnetic resonance occurs in an MRI scanner, a magnetic field gradient for imaging must be established. Therefore, development/research conducted by companies that produce and sell most existing MRI scanners has been focused on schemes for causing a gradient field to have a stronger gradient in a given space. For example, current medical MRI scanners for hospitals have been developed in such a way that the strengths of a magnetic field are 1.5 T, 3 T, 7 T, . . . . However, a problem may arise in that, in order to increase the strength of a magnetic field per unit area against very high power corresponding to several tens of amperes (A) to several hundreds of amperes (several Kw to several tens of Kw), expensive liquid helium and a superconductor coil must be manufactured. Also, when the frequency and the strength of a magnetic field are decreased, the strength of a linear gradient field formed in space is decreased, and thus only a very small sample can be measured.

PRIOR ART DOCUMENTS

Patent Documents (Patent Document 1) U.S. Pat. No. 9,977,764, Date of Registration: May 22, 2018, Title: "Method for designing coil systems for generation of magnetic fields of desired geometry, a magnetic resonance imaging or magnetoencephalography apparatus with a coil assembly and a computer program"

(Patent Document 2) Japanese Patent Application Publication No. JP 2002-291716, Date of Publication: Oct. 8, 2002, Title: "Magnetic Resonance Imaging (MRI) Scanner Equipped with Higher-Order Encoding Gradient Magnetic Field Coil"

SUMMARY OF THE INVENTION

Accordingly, the present invention has been made keeping in mind the above problems occurring in the prior art, and an object of the present invention is to provide a magnetic-field-generating coil system that has low power consumption and can be implemented at low cost, an imaging system having the magnetic-field-generating coil system, and a method for operating the imaging system.

In accordance with an aspect of the present invention to accomplish the above object, there is provided a magnetic-field-generating coil system, including a first coil configured to generate a first magnetic field in a first direction; a second coil arranged to face the first coil and configured to generate a second magnetic field in the first direction; a first power source configured to supply a first current to the first coil; a second power source configured to supply a second current to the second coil; and a current controller configured to control amounts of the first current and the second current so that a Linear Gradient Field (LGF) is generated or moved by the first magnetic field and the second magnetic field.

In an embodiment, each of the first coil and the second coil may be implemented as any one of a solenoid coil, an electromagnet coil, a Helmholtz coil, and a Maxwell coil.

In an embodiment, each of the first coil and the second coil may include a coil part for acquiring a Magnetic Resonance Imaging (MRI) signal, a coil part for forming a gradient magnetic field for each axis, at least one coil part for applying a Radio Frequency (RF) pulse having a spin echo, and a coil part for finely adjusting a magnetic field.

In an embodiment, a spatial position of the LGF may be determined based on a transfer function having the amounts of the first and second currents and positions of the first and second magnetic fields as variables.

In accordance with another aspect of the present invention to accomplish the above object, there is provided a method for operating a Magnetic Resonance Imaging (MRI) system, including generating multiple Linear Gradient Fields (LGFs) in respective axial directions by controlling coil currents; and acquiring MRI information or Magnetic Particle Imaging (MPI) information about an object while moving the multiple LGFs by varying the coil currents.

In an embodiment, a first coil and a second coil arranged to face the first coil may be included in each of the axial directions, and independent currents may be supplied to the first and second coils, respectively.

In an embodiment, generating the multiple LGFs may include controlling currents flowing through the first and second coils.

In an embodiment, acquiring the MRI information or the MPI information may include detecting a Free Induction Delay (FID) signal from the multiple LGFs.

In an embodiment, the method may further include generating K-spaces for respective multiple LGFs.

In an embodiment, pieces of relative position information of the respective multiple LGFs may be determined based on a transfer function that has amounts of currents flowing through coils and positions of generated magnetic fields as variables.

In an embodiment, the method may further include configuring an image of the object by adding the pieces of relative position information to the K-spaces.

In an embodiment, the method may further include scanning the object while moving the multiple LGFs.

In an embodiment, acquiring the MRI information or the MPI information may include blocking power to be applied to each axis in a magnetic field space formed in a three-dimensional (3D) space; applying a magnetic field using a coil part for applying a RF pulse; and acquiring an MRI signal using a coil part located in a direction perpendicular to a direction in which the magnetic field is applied.

In an embodiment, acquiring the MRI information or the MPI information may include sequentially blocking power to be applied to individual axes in a magnetic field space formed in a three-dimensional (3D) space; applying and measuring an RF pulse for generating a spin echo, using a coil part on any one axis arranged in a direction perpendicular to any one power-blocked axis; and acquiring an MRI signal, using a coil part on a remaining one axis arranged in the direction perpendicular to the any one power-blocked axis.

In accordance with a further aspect of the present invention to accomplish the above object, there is provided an imaging system, including an image scan device for acquiring a detection signal corresponding to Magnetic Resonance Imaging (MRI) information or Magnetic Particle Imaging (MPI) information about an object; a spectrum signal generation device for transforming the detection signal into a detection spectrum signal; an image recovery device for generating an image signal for the object based on the detection spectrum signal and a system function; and a display device for displaying the image signal, wherein the image scan device includes a coil system configured to generate multiple Linear Gradient Fields (LGFs) in respective axial directions by controlling coil currents; and acquire the detection signal for the object while moving the multiple LGFs by varying the coil currents.

In an embodiment, the coil system may include a first coil configured to generate a first magnetic field in a first axial direction; a second coil arranged to face the first coil and configured to generate a second magnetic field in the first axial direction; a first power source configured to supply a first current to the first coil; a second power source configured to supply a second current to the second coil; and a current controller configured to control amounts of the first current and the second current so that an LGF is generated or moved by the first magnetic field and the second magnetic field.

In an embodiment, the detection signal may include a Free Induction Delay (FID) signal detected from the multiple LGFs.

In an embodiment, the image scan device may scan the object while moving the multiple LGFs.

In an embodiment, the coil system may be provided in each of directions of an X axis, a Y axis, and a Z axis, which are orthogonal to each other.

In an embodiment, the image recovery device may fix additional coordinates generated by moving LGFs using a function that is based on amounts of currents to be applied to the first and second coils and strengths of the generated LGFs.

In an embodiment, the image recovery device may finally configure an image of the object by adding the fixed coordinates to pieces of position information acquired for respective K-spaces configuring the LGFs.

BRIEF DESCRIPTION OF THE DRAWINGS

The accompanying drawings are provided to help the understanding of the present embodiments, and the embodiments are provided together with the detailed descriptions thereof. However, the technical features of the present embodiments are not limited to what is specifically shown in the drawings, and the features disclosed in respective drawings may be combined to configure new embodiments.

DESCRIPTION OF THE PREFERRED EMBODIMENTS

Figure 1A:
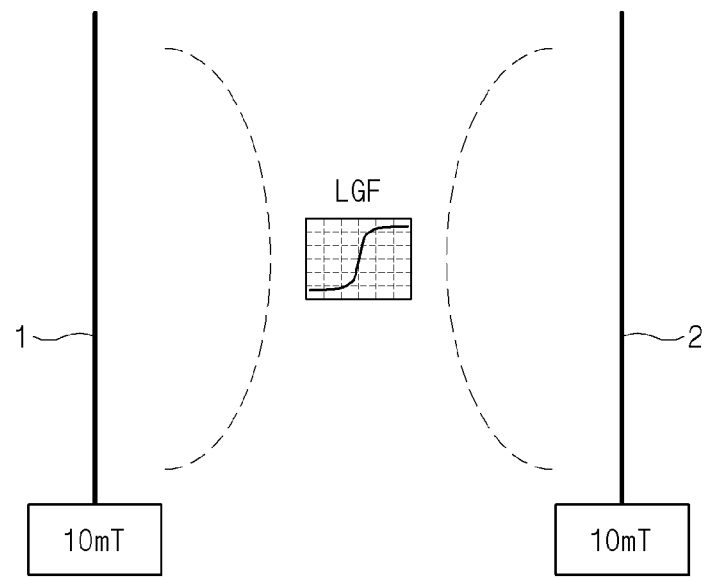
FIGS. 1A, 1B, and 1C are diagrams for conceptually explaining a scheme for generating and moving a Linear Gradient Field (LGF) according to an embodiment of the present invention.

Embodiments of the present invention are described with reference to the accompanying drawings in order to describe the present invention in detail so that those having ordinary knowledge in the technical field to which the present invention pertains can easily practice the present invention.

Reference will now be made in detail to various embodiments of the present invention, specific examples of which are illustrated in the accompanying drawings and described below, since the embodiments of the present invention can be variously modified in many different forms. However, this is not intended to limit the present invention to particular modes of practice, and it is to be appreciated that all changes, equivalents, and substitutes that do not depart from the spirit and technical scope of the present invention are encompassed in the present invention. It will be understood that, although the terms "first" and "second" may be used herein to describe various elements, these elements should not be limited by these terms. These terms are only used to distinguish one element from another element. For instance, a first element discussed below could be termed a second element without departing from the teachings of the present invention. Similarly, the second element could also be termed the first element. It will be understood that when an element is referred to as being "coupled" or "connected" to another element, it can be directly coupled or connected to the other element, or intervening elements may be present therebetween. In contrast, it should be understood that when an element is referred to as being "directly coupled" or "directly connected" to another element, there are no intervening elements present.

The terminology used herein is for the purpose of describing particular embodiments only and is not intended to be limiting. In the present invention, the singular forms are intended to include the plural forms as well, unless the context clearly indicates otherwise. It should be further understood that the terms "comprise", "include", and "have", when used in this specification, specify the presence of stated features, integers, steps, operations, elements, components, and/or combinations thereof, but do not preclude the presence or addition of one or more other features, integers, steps, operations, elements, components, and/or combinations thereof. Unless differently defined, all terms used here including technical or scientific terms have the same meanings as terms generally understood by those skilled in the art to which the present invention pertains. Terms identical to those defined in generally used dictionaries should be interpreted as having meanings identical to contextual meanings of the related art, and are not to be interpreted as having ideal or excessively formal meanings unless they are definitely defined in the present specification.

An imaging system and a method for operating the imaging system according to an embodiment of the present invention may include the step of generating multiple Linear Gradient Fields (LGF) in the directions of respective axes, that is, in respective axial directions, by controlling coil currents and the step of acquiring Magnetic Resonance Imaging (MRI) information and Magnetic Particle Imaging (MPI) information about an object while varying the coil currents and moving the multiple LGFs. In this way, the imaging system may be implemented at low power consumption and at low cost.

Figure 1B:
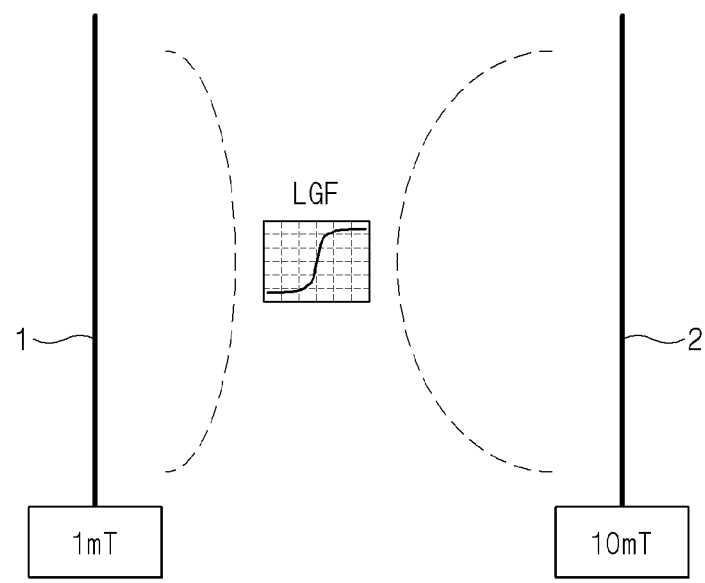
Figure 1C:
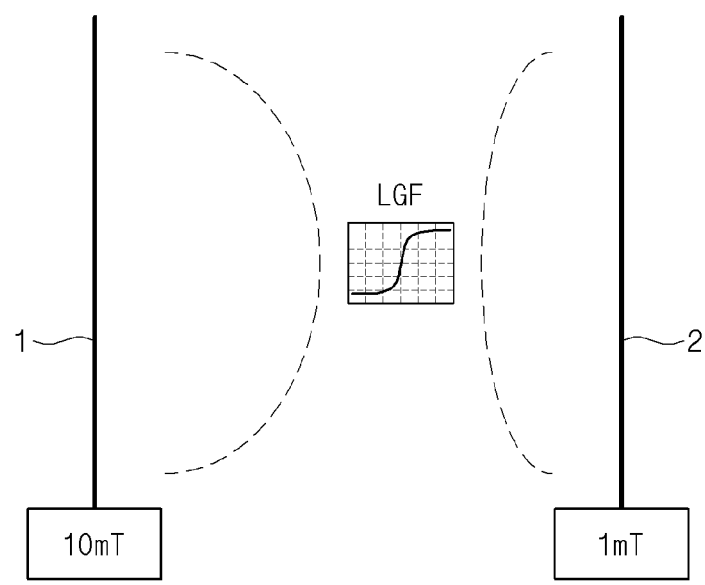

FIGS. 1A, 1B, and 1C are diagrams for conceptually explaining a scheme for generating and moving a Linear Gradient Field (LGF) according to an embodiment of the present invention. Referring to FIG. 1A, when opposing (facing) coils 1 and 2 radiate electromagnetic signals at the same magnetic field strength (e.g. 10 mT), an LGF may be formed at a center portion between the coils 1 and 2. Referring to FIG. 1B, when the magnetic field strength of an electromagnetic signal radiated from a right coil 2 is greater than that of a left coil 1 (e.g. 10 mT>1 mT), an LGF may be moved from the center and formed closer to the left coil 1. In contrast, referring to FIG. 1C, when the magnetic field strength of an electromagnetic signal radiated from a right coil 2 is less than that of a left coil 1 (e.g. 1 mT<10 mT), an LGF may be moved from the center and formed closer to the right coil 2.

In summary, as illustrated in FIGS. 1A, 1B, and 1C, the LGF may be moved by adjusting the strengths of magnetic fields of the electromagnetic signals radiated from the opposing coils 1 and 2.

Figure 2:
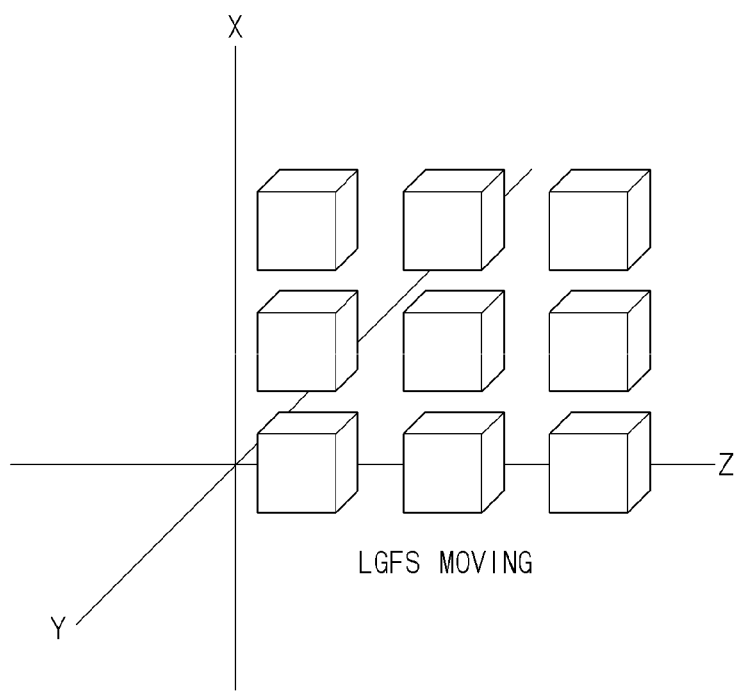
FIG. 2 is a diagram for conceptually explaining the operation of an imaging system according to an embodiment of the present invention.

FIG. 2 is a diagram for conceptually explaining the operation of an imaging system according to an embodiment of the present invention. Referring to FIG. 2, unlike a typical imaging system which forms a single static gradient field in space, the imaging system according to an embodiment of the present invention may acquire a Magnetic Resonance (MR) signal by moving small LGFs.

The imaging system according to the embodiment of the present invention may replace an expensive MRI magnetic field system which uses a large-sized magnetic field coil or superconductor, and may have a small size, but may acquire an image of an object having a relatively large width (or a relatively large volume).

Figure 3:
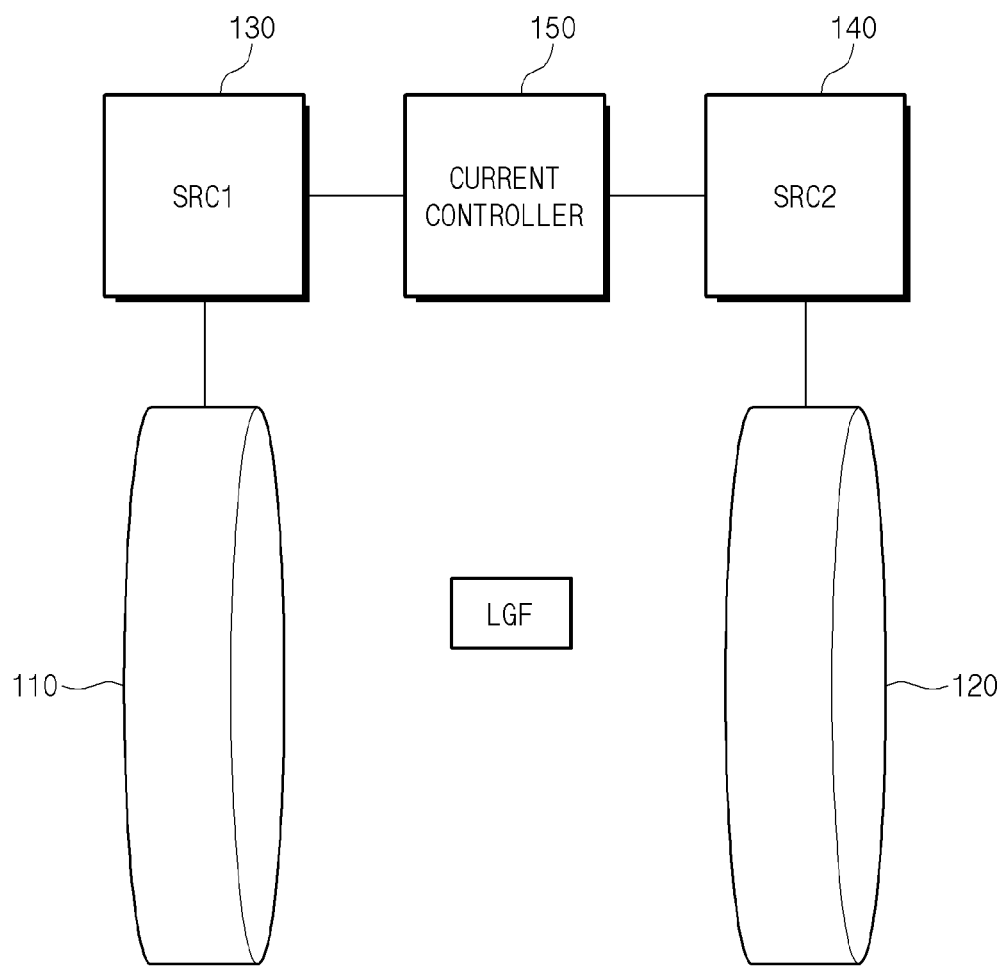
FIG. 3 is a diagram exemplarily illustrating a magnetic-field-generating coil system which is applicable to an imaging system according to an embodiment of the present invention.

FIG. 3 is a diagram exemplarily illustrating a magnetic-field-generating coil system 100 which is applicable to an imaging system according to an embodiment of the present invention. Referring to FIG. 3, the magnetic-field-generating coil system 100 may include a first coil 110, a second coil 120, a first power source SRC1 130, a second power source SRC2 140, and a current controller 150. In an embodiment, the magnetic-field-generating coil system 100 may correspond to any one of axial directions of the imaging system.

The first coil 110 and the second coil 120 may be arranged to oppose (face) each other in any one of the axial directions of the imaging system. Each of the first coil 110 and the second coil 120 may be a solenoid coil or an electromagnet coil. However, it should be noted that the first coil 110 and the second coil 120 are not limited thereto.

The first power source 130 may be configured to supply a first current to the first coil 110. Here, the strength of a first magnetic field radiated from the first coil 110 may be determined depending on the magnitude of the first current.

The second power source 140 may be configured to supply a second current to the second coil 120. Here, the strength of a second magnetic field radiated from the second coil 120 may be determined depending on the magnitude of the second current.

The current controller 150 may be configured to control the magnitudes of the currents output from the first and second power sources 130 and 140.

The magnetic-field-generating coil system 100 according to the embodiment of the present invention may generate and move an LGF by controlling the currents flowing through the coils 110 and 120, which are arranged to face each other. The magnetic-field-generating coil system 100 may continuously move homogeneous magnetic fields because it is capable of controlling the supply of power to each axis.

Below, the fixing of coordinates of a small LGF will be described. When an LGF is moved, the position of the LGF may be detected by acquiring the coordinates of the position without using a complicated mathematical function because, unlike a conventional scheme, different currents are supplied to respective axes, and then the amounts of currents supplied to respective axes may become respective coordinates in space.

Figure 4:
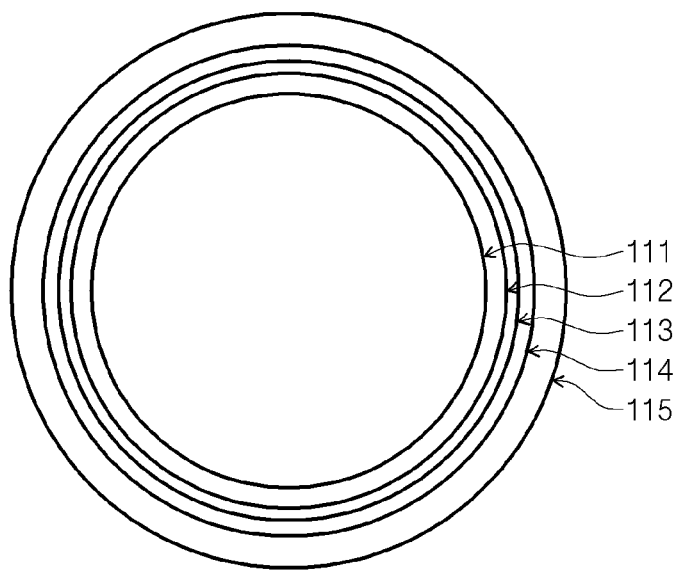
FIG. 4 is a diagram exemplarily illustrating a first coil according to an embodiment of the present invention.

FIG. 4 is a diagram exemplarily illustrating a first coil 110 according to an embodiment of the present invention. Referring to FIG. 4, the first coil 110 may include a first coil part 111, a second coil part 112, a third coil part 113, a fourth coil part 114, and a fifth coil part 115.

The first coil part 111 may be a coil for acquiring an MRI signal (or a Free-Induction Delay (FID) signal).

The second coil part 112 may be a coil for forming a gradient magnetic field for each axis.

The third coil part 113 may be a coil for applying an RF pulse having a first spin echo. Here, the angle of the first spin echo may be 90°.

The fourth coil part 114 may be a coil for applying an RF pulse having a second spin echo. Here, the angle of the second spin echo may be 180°.

The fifth coil part 115 may be a coil for acquiring an MRI signal or finely adjusting a magnetic field if necessary. For example, the fifth coil part 115 may be a shimming coil.

Meanwhile, the configuration of the second coil 120 may also be implemented in the same manner as the first coil 110.

Figure 5:
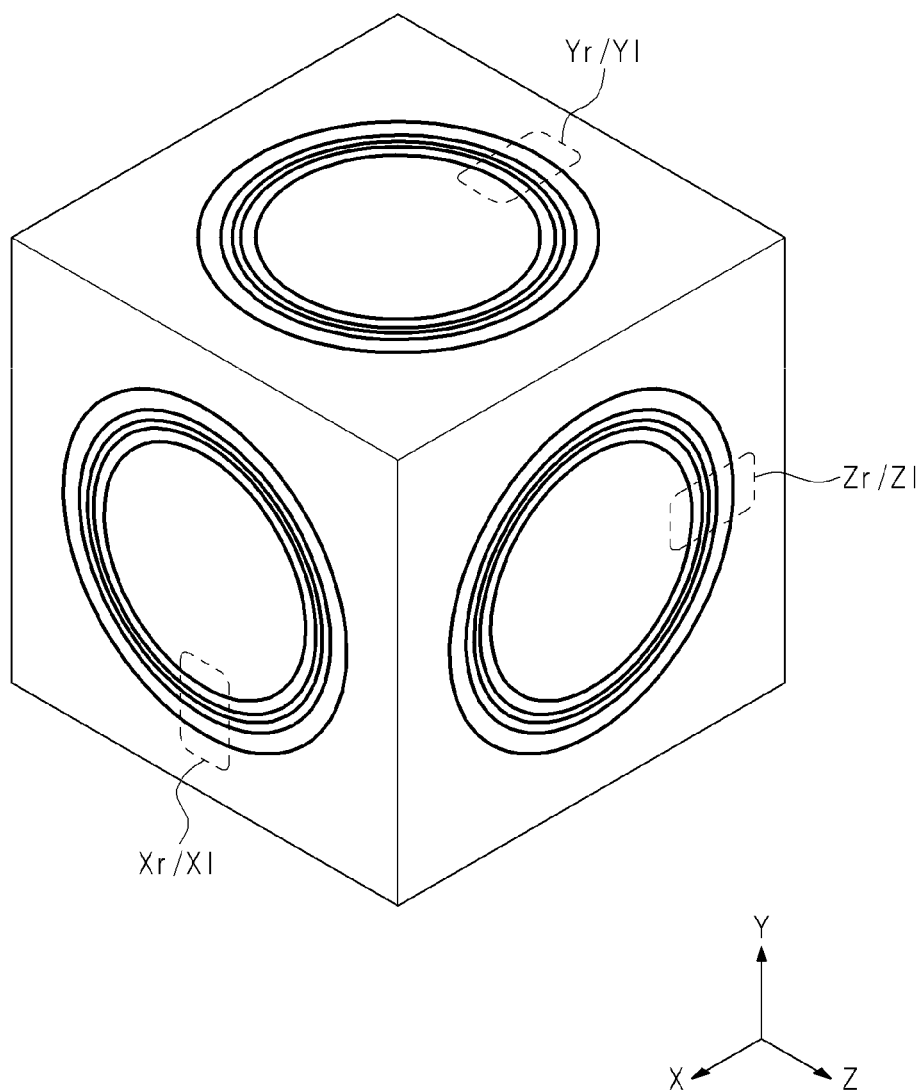
FIG. 5 is a diagram exemplarily illustrating a coil for forming a magnetic field in a three-dimensional (3D) space according to an embodiment of the present invention.

FIG. 5 is a diagram exemplarily illustrating a coil for forming a magnetic field in a 3D space according to an embodiment of the present invention.

Figure 6:
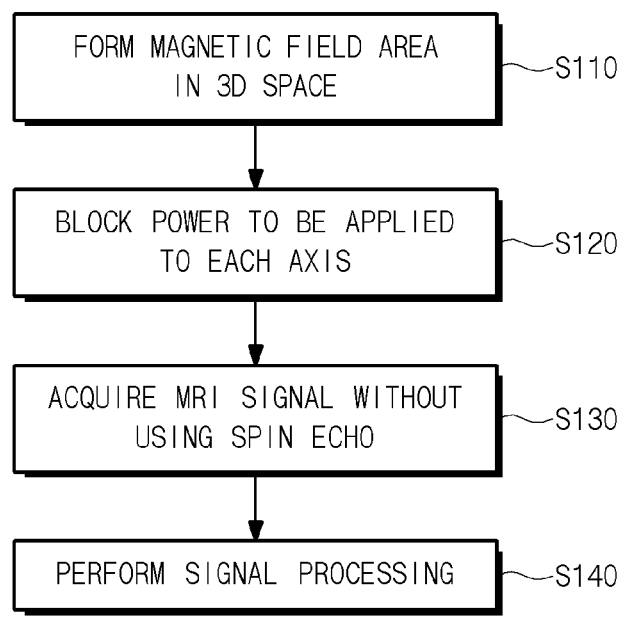
FIG. 6 is a flowchart exemplarily illustrating a process for acquiring an MRI signal without using a spin echo (RF signal) according to an embodiment of the present invention.

FIG. 6 is a flowchart exemplarily illustrating a process for acquiring an MRI signal without using a spin echo (RF signal) according to an embodiment of the present invention. Referring to FIG. 6, the process for acquiring an MRI signal without using a spin echo may be performed as follows.

As illustrated in FIG. 5, a desired magnetic field area may be formed in a 3D space using axial magnetic field coils on XYZ axes at step S110. For example, when a description is made based on a first axis, a magnetic field space of 0.1 mT may be formed in a 3D space (X Y Z) when a current of 1 A and a current of 1.5 A are applied to Zr and Zl, respectively, a current of 2 A and a current of 0.5 A are applied to Xr and Xl, respectively, and a current of 3 A and a current of 1 A are applied to Yr and Yl, respectively.

In this state, the power to be supplied to each axis may be blocked at step S120. Here, a procession of hydrogen atomic nuclei may be initiated while hydrogen atomic nuclei aligned in the axial direction of a magnetic field resonate only when the supply of power is blocked. When a hydrogen atomic nucleus, which is the origin of an actual MRI signal, is present in a desired space, a signal attributable to the procession of the hydrogen atomic nucleus may be produced based on a Larmor frequency formula. Since a spin echo is not used, an MRI signal may be acquired using a coil located in a direction perpendicular to the direction in which coil parts 113 and 114 for RF pulses illustrated in FIG. 4 apply magnetic fields at step S130.

Thereafter, the acquired MRI signal may be finally signal-processed by being subjected to a Fast Fourier Transform (FFT) after passing through a fast digitizer for increasing the Q-factor of the MRI signal, a low-noise amplifier, and a bandwidth filter at step S140.

Meanwhile, the above-described processes are repeated while varying the strength of a magnetic field in space, and thus the magnetic field in the space may be transformed into K-space data.

Figure 7:
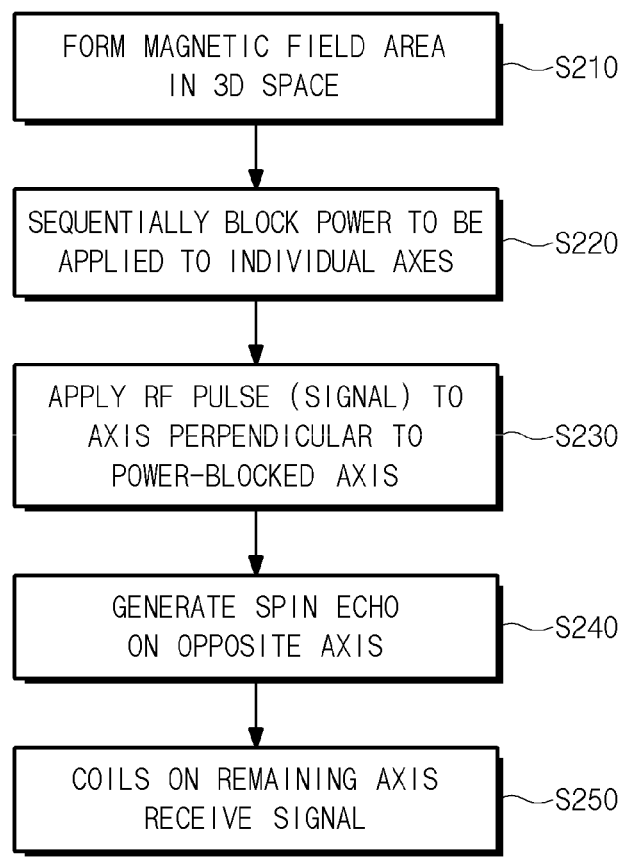
FIG. 7 is a flowchart illustrating a process for acquiring an MRI signal using a spin echo according to an embodiment of the present invention.

FIG. 7 is a flowchart illustrating a process for acquiring an MRI signal using a spin echo according to an embodiment of the present invention. Referring to FIG. 7, the process for acquiring an MRI signal using a spin echo may be performed as follows.

As illustrated in FIG. 5, a desired magnetic field area may be formed in a 3D space using axial magnetic field coils on XYZ axes at step S210. For example, when a description is made based on a first axis, a magnetic field space of 0.1 mT may be formed in a 3D space (X Y Z) when a current of 1 A and a current of 1.5 A are applied to Zr and Zl, respectively, a current of 2 A and a current of 0.5 A are applied to Xr and Xl, respectively, and a current of 3 A and a current of 1 A are applied to Yr and Yl, respectively.

In this state, the power to be supplied to individual axes may be sequentially blocked at step S220. The sequence of the XYZ axes in which power is to be blocked does not matter, but for subsequent position detection the sequence of XYZ axes in which power has been blocked needs only to be checked. When it is desired to identify the position for each axis, only the power for the corresponding axis may be blocked.

Among the power-blocked axes XYZ, one of two perpendicularly arranged axes, that is, one of XY axes, may be taken. For example, an RF pulse may be applied from an RF coil corresponding to Yr in the direction at 90° at step S230. Here, the frequency of the RF pulse may be a Larmor frequency.

A spin echo wave of 180° may be generated from a coil (i.e. an opposite coil) on the opposite side of the same axis, that is, an RF coil corresponding to Yl, at step S240.

Meanwhile, the RF coil used herein may be any one of the third coil part 113 and the fourth coil part 114, as illustrated in FIG. 4. The remaining coil may be used to generate an RF pulse. The coils on the remaining one axis of the XY axes may be used as receiving coils. For example, when the Z axis is turned off and the Y axis is used as the axis for generating and measuring a pulse for a spin echo, the X axis may be the remaining one axis. Here, the coils on the X axis may be used as receiving coils for acquiring an MRI signal at step S250. The coils used at this time may be the first coil part 111 and the fifth coil part 115.

Meanwhile, the above-described processes may be repeated while varying the strength of a magnetic field in space, and thus the magnetic field in space may be transformed into K-space data.

Figure 8:
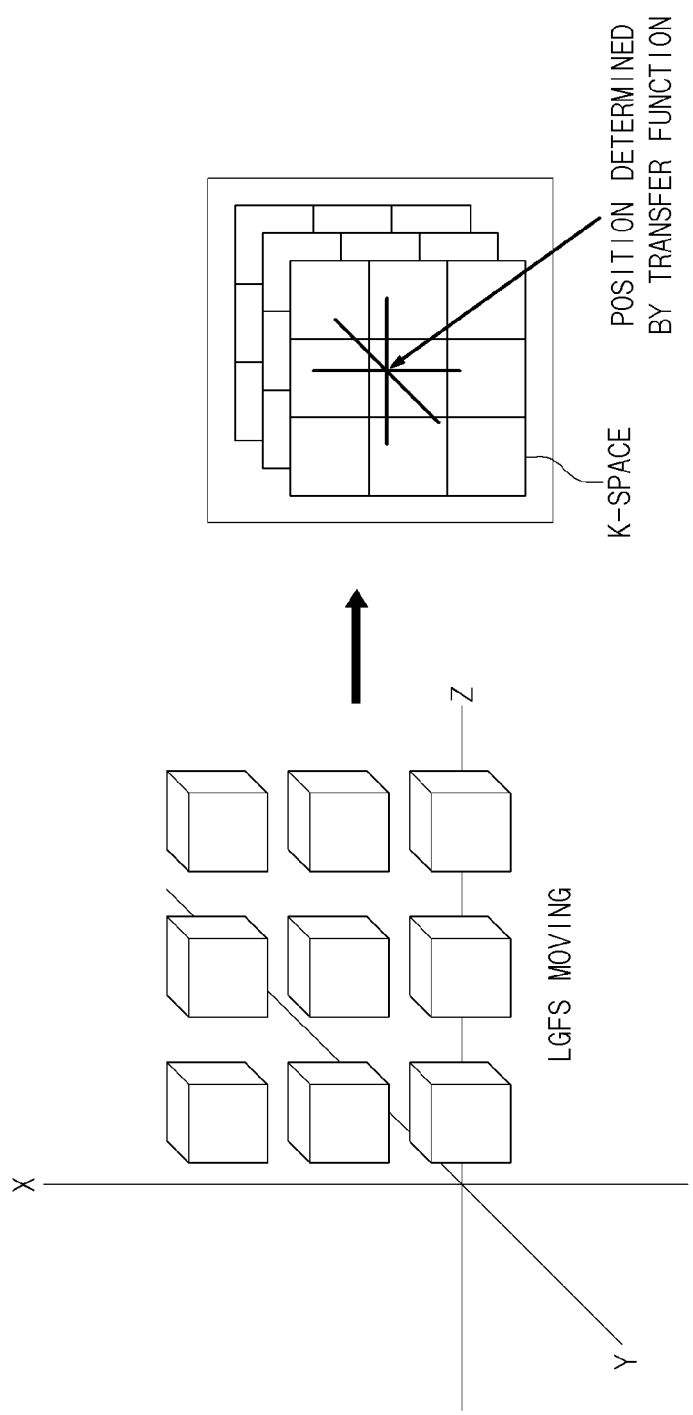
FIG. 8 is a diagram for explaining a coordinate determination scheme for configuring an image in an imaging system according to an embodiment of the present invention.

FIG. 8 is a diagram for explaining a coordinate determination scheme for configuring an image in an imaging system according to an embodiment of the present invention.

The imaging system according to the embodiment of the present invention may measure in advance the amounts of currents applied to respective axes (and thus the relative strengths of LGFs formed in space), together with the use of a method using the Larmor equation, may create a transfer function using the amounts of currents, and may then acquire positions related to the movement of the LGFs.

Referring to FIG. 8, the configuration of a Magnetic Resonance (MR) image is described below. Two types of MR image information acquired in different manners may be reconstructed using a transfer function that is based on pieces of MR information (chiefly Free Induction Delay (FID) signals) acquired from respective LGFs and currents flowing through the magnetic-field-generating coil system 100 (see FIG. 3) (or the positions of generated magnetic fields in space).

In an embodiment, for a K-space for each LGF, the relative spatial position of each LGF may be determined by a transfer function having the amount of current applied to the corresponding coil and the position of a generated magnetic field as variables. Here, the K-space may be a set of raw data that can constitute a single image.

Figure 9:
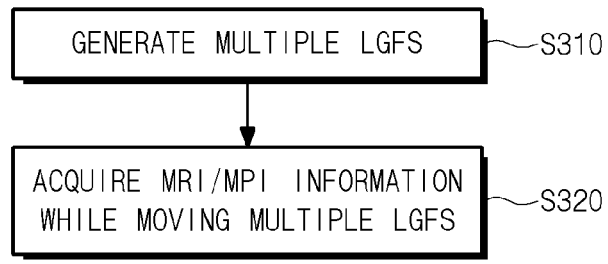
FIG. 9 is a flowchart exemplarily illustrating a method for operating an imaging system according to an embodiment of the present invention.

FIG. 9 is a flowchart exemplarily illustrating a method for operating an imaging system according to an embodiment of the present invention. Referring to FIGS. 1 to 9, the method for operating an imaging system will be described below. Multiple LGFs may be generated by controlling coil currents in respective axial directions of the imaging system at step S310. Here, it should be noted that the sizes and directions of the generated LGFs are not particularly limited.

The generated LGFs may be moved by varying the coil currents to be applied in respective axial directions of the imaging system. Here, Magnetic Resonance Imaging (MRI)/Magnetic Particle Imaging (MPI) information about an object may be acquired using a signal detector (not illustrated) at step S320. The relative positions of respective LGFs in the K-space may be determined using the transfer function, which has, as variables, the amounts of currents flowing through the coils and the positions of magnetic fields, and MRI/MPI information about the object may be acquired based on the relative positions of respective LGFs.

In accordance with an embodiment, some or all of steps and/or operations may be at least partially implemented or executed using instructions, programs and interactive data structures stored in one or more non-transitory computer-readable storage media, and one or more processors for driving clients and/or servers. Examples of such computer-readable storage media include all types of hardware devices (volatile/nonvolatile memory) particularly configured to store and execute program instructions, such as magnetic media, such as a hard disk, a floppy disk, and magnetic tape, optical media, such as compact disk (CD)-read only memory (ROM) and a digital versatile disk (DVD), magneto-optical media, such as a floptical disk, ROM, Random Access Memory (RAM), and flash memory. The one or more non-transitory computer-readable storage media may be, for example, software, firmware, or hardware, and/or any combination thereof. Also, the function of the term "module" discussed in the present specification may be implemented using software, firmware, hardware and/or combinations thereof.

The one or more non-transitory computer-readable storage media and/or means for implementing/executing one or more operations/steps/modules according to embodiments of the present invention may include, but are not limited to, Application-Specific Integrated Circuits (ASICs), standard Integrated Circuits, controllers which include a microcontroller and execute suitable commands, and/or embedded controllers, Field-Programmable Gate Arrays (FPGAs), Complex Programmable Logic Devices (CPLDs), etc.

Meanwhile, the present invention may also be applied to an MPI system.

Figure 10:
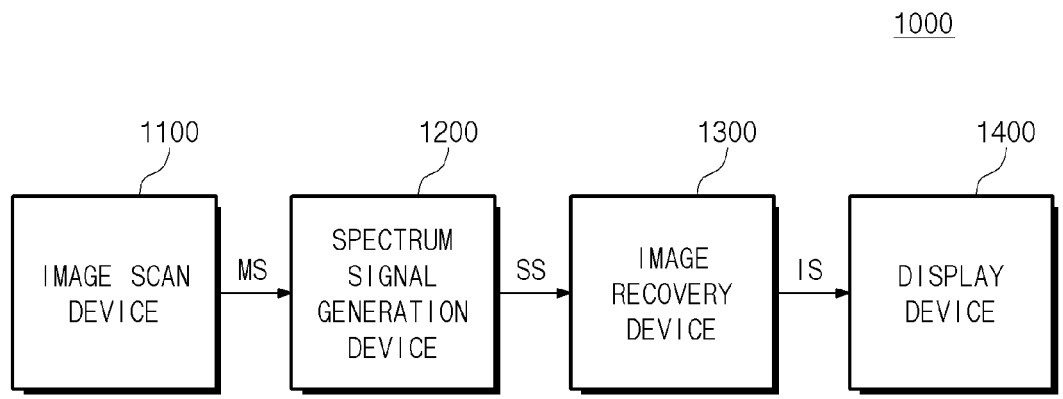
FIG. 10 is a diagram exemplarily illustrating an imaging system according to an embodiment of the present invention.

FIG. 10 is a diagram exemplarily illustrating an imaging system according to an embodiment of the present invention. Referring to FIG. 10, an imaging system 1000 may include an image scan device 1100, a spectrum signal generation device 1200, an image recovery device 1300, and a display device 1400. The imaging system 1000 may acquire an image of a specific article or object.

The image scan device 1100 may be configured to acquire a detection signal MS corresponding to MRI/MPI information about the object. The image scan device 1100 may acquire the detection signal MS corresponding to the MRI/MPI information while moving LGFs, described above with reference to FIGS. 1 to 5. The image scan device 1100 may generate multiple LGFs in respective axial directions by controlling coil currents, and may acquire Magnetic Resonance Imaging (MRI) information or Magnetic Particle Imaging (MPI) information about the object by varying the coil currents and then moving the multiple LGFs.

The image scan device 1100 may provide an Alternating Current (AC) magnetic field to the object. The image scan device 1100 may generate the detection signal MS based on an induced magnetic field, which is induced from magnetic particles formed on the object. The image scan device 1100 may use the magnetic particles as a tracer. The image scan device 1100 may provide an AC magnetic field to the magnetic particles contained in a contrast medium, and the magnetic particles may generate an induced magnetic field, which is induced by the AC magnetic field. The image scan device 1100 may detect the induced magnetic field.

The image scan device 1100 may detect the induced magnetic field formed in a detection area. The detection area may be formed under the control of the image scan device 1100. The image scan device 1100 may detect the induced magnetic field using a Lissajous scan scheme. The image scan device 1100 may detect the induced magnetic field generated from magnetic particles formed at a specific position along a Lissajous trajectory. An electric field may be induced based on the induced magnetic field generated from the magnetic particles. That is, the detection signal MS may be the induced electric field. The detection signal MS may indicate a voltage value applied to the image scan device 1100 over time.

The spectrum signal generation device 1200 may be configured to receive the detection signal MS from the image scan device 1100. The spectrum signal generation device 1200 may transform the detection signal MS into a detection spectrum signal SS. The spectrum signal generation device 1200 may transform the detection signal MS into the detection spectrum signal SS using a two-dimensional (2D) Fourier transform kernel. That is, the detection signal MS may be an electrical signal in a time domain, and the detection spectrum signal SS may be an electrical signal in a frequency domain.

The spectrum signal generation device 1200 may generate the detection spectrum signal SS through the 2D Fourier transform. The 2D Fourier transform kernel may be a matrix for performing a Fourier transform on the detection signal MS. The detection signal MS may be transformed into the form of a column vector over time. The detection spectrum signal SS may be formed by a matrix multiplication of the 2D Fourier transform kernel and the detection signal MS transformed into the column vector.

The spectrum signal generation device 1200 may include an Analog-to-Digital Converter (ADC) for converting the detection signal MS, which is an electrical signal, into a digital signal. The ADC may digitize the detection signal MS into a discrete value by converting the detection signal MS into a digital signal. The detection signal MS may be converted into a column vector for vector operations based on the digitized discrete value. However, the present invention is not limited thereto, and the spectrum signal generation device 1200 may generate the detection spectrum signal SS using the analog signal.

The spectrum signal generation device 1200 may generate a system function. The system function may be used to map the detection spectrum signal SS and a magnetic particle distribution to each other in order to perform image recovery. The system function may be generated based on various variables, such as the magnetization characteristics of magnetic particles, the geometry of the image scan device 1100, or an image acquisition condition. Similar to the detection spectrum signal SS, the system function may be generated using the 2D Fourier transform kernel.

The spectrum signal generation device 1200 may generate the system function by transforming a signal, measured by directly and spatially scanning the magnetic particles. However, the present invention is not limited thereto, and the system function may be generated based on a mathematical model, such as the bases of Chebyshev polynomials and convolution with the differentiation of a Langevin function.

The spectrum signal generation device 1200 may perform a matrix operation using the 2D Fourier transform kernel. The spectrum signal generation device 1200 may include an electronic circuit for performing such a matrix operation. For example, the spectrum signal generation device 1200 may include storage for storing element values of the 2D Fourier transform kernel and a multiplier for performing a matrix multiplication. However, the present invention is not limited thereto, and the spectrum signal generation device 1200 may acquire a detection signal MS over time, and may generate a detection spectrum signal SS through a software operation under the control of the processor. Although the spectrum signal generation device 1200 illustrated in FIG. 10 is provided as a separate component, the configuration of the present invention is not limited thereto, and the spectrum signal generation device 1200 may also be included in the image recovery device 1300.

The image recovery device 1300 may be configured to receive the detection spectrum signal SS from the spectrum signal generation device 1200. The image recovery device 1300 may receive the system function from the spectrum signal generation device 1200. The image recovery device 1300 may generate an image signal IS based on the detection spectrum signal SS and the system function. The image recovery device 1300 may reconstruct an image of the detected object based on the detection spectrum signal SS and the system function.

The display device 1400 may receive the image signal IS from the image recovery device 1300. The display device 1400 may generate a data voltage based on the image signal IS, and may display an image based on the data voltage. For example, the display device 1400 may include a Liquid Crystal Display (LCD), an Organic Light-Emitting Diode (OLED), an Active Matrix OLED (AMOLED), a flexible display, electronic ink, etc.

Figure 11:
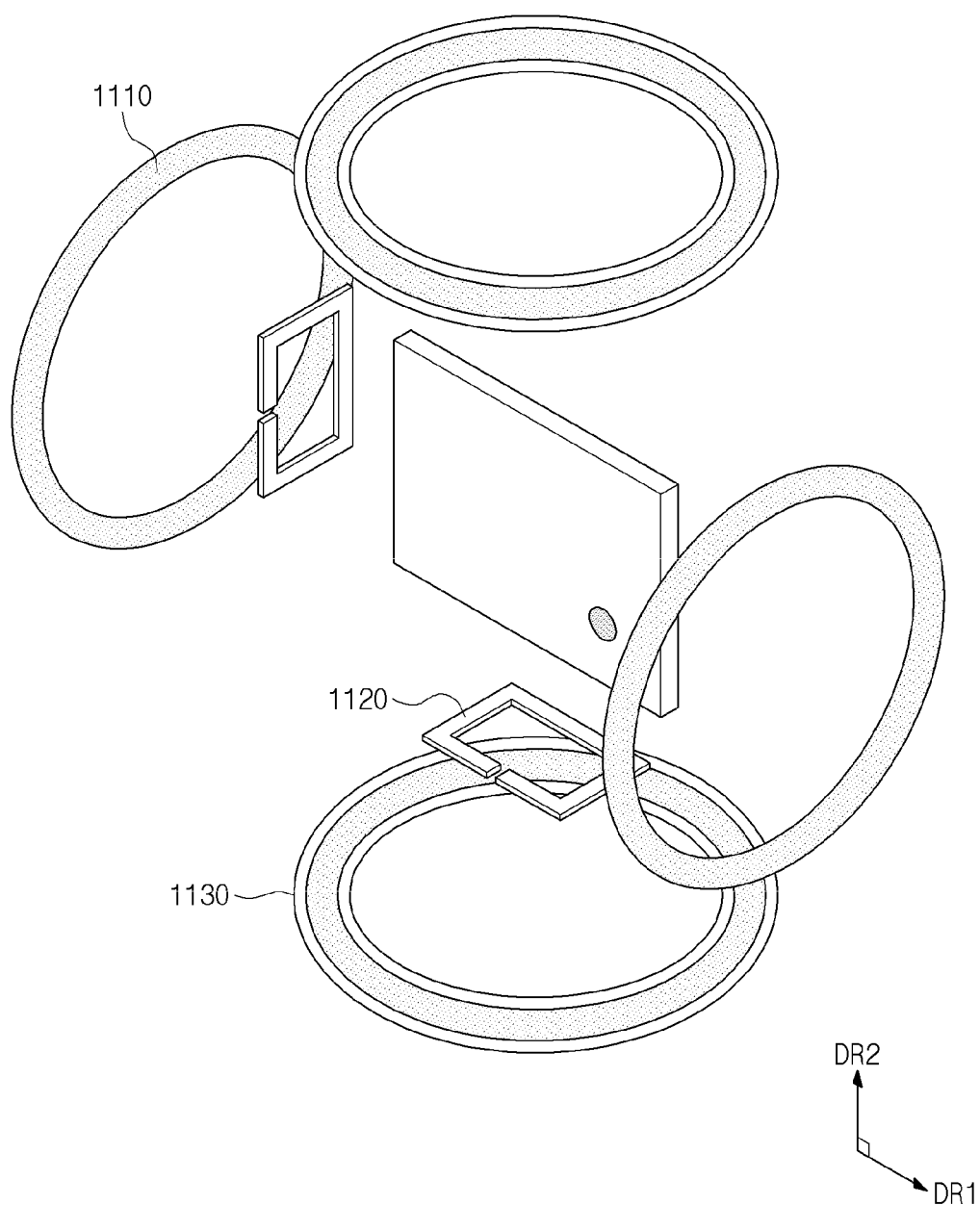
FIG. 11 is a diagram exemplarily illustrating the image scan device of FIG. 10.

FIG. 11 is a diagram exemplarily illustrating the image scan device 1100 of FIG. 10. Referring to FIG. 11, the image scan device 1100 may include a magnetic field provider 1110, an induced signal detector 1120, and a scan controller 1130.

The image scan device 1100 may be configured to detect magnetic particles arranged therein. A scan trajectory required by the image scan device 1100 to detect magnetic particles may be parallel to a plane formed between a first direction DR1 and a second direction DR2. The first direction DR1 and the second direction DR2 may be orthogonal to each other.

The magnetic field provider 1110 may be configured to provide an AC magnetic field to the magnetic particles. The AC magnetic field may have a specific frequency. The magnetic field provider 1110 may apply a first AC magnetic field in the first direction DR1. The magnetic field provider 1110 may include a first driving coil for applying the first AC magnetic field in the first direction DR1. The first driving coil may include multiple coils arranged to face each other in the first direction DR1, with an object interposed therebetween. The first driving coil may be, but is not limited to, a ring-type coil. When the first driving coil is a ring-type coil, an AC magnetic field may be formed based on the flow of current through the first driving coil.

The induced signal detector 1120 may be configured to detect an induced magnetic field that is induced from magnetic particles. The induced magnetic field may be generated from the magnetic particles due to the AC magnetic field. For example, the magnetic particles may have nonlinear magnetization characteristics. An induced magnetic field signal may be generated due to the nonlinear magnetization characteristics of the magnetic particles. The induced signal detector 1120 may include an induction coil for detecting the induced magnetic field. The induction coil may have a first induction coil and a second induction coil. The first induction coil may detect an induced magnetic field in the first direction DR1. The second induction coil may detect an induced magnetic field in the second direction DR2. The first induction coil may be arranged to be spaced apart from the object in the first direction DR1. The second induction coil may be arranged to be spaced apart from the object in the second direction DR2.

The induced signal detector 1120 may be configured to generate a detection signal MS by detecting an induced magnetic field. The detection signal MS may be an electrical signal that is generated based on variation in the induced magnetic field. The induced signal detector 1120 may have the shape of a coil for inducing an electrical signal. The induced signal detector 1120 may provide the detection signal MS to the spectrum signal generation device 1200.

The scan controller 1130 may control a detection area for the induced magnetic field. The detection area may be defined as a measurement area (i.e., a field of view) in which the image scan device 1100 detects the induced magnetic field of magnetic particles. The scan controller 1130 may form a local area lacking a magnetic field (i.e. a field-free point) so that the magnetization characteristics of the magnetic particles can be observed. The detection area may be formed in the local area. The scan selector 1130 may include a selection coil for forming the local area. The selection coil may include multiple coils arranged to face each other in the second direction DR2, with the object interposed therebetween. The selection coil may be, but is not limited to, a ring-type coil. When the selection coil has two coils, one coil may apply a current in a clockwise direction, and the other coil may apply a current in a counterclockwise direction. In this case, since magnetic fields having the same polarity face each other, a local area lacking a magnetic field may be formed.

The scan controller 1130 may include a second driving coil for applying a second AC magnetic field in the second direction DR2. The second driving coil may include multiple coils arranged to face each other in the second direction DR2, with the object interposed therebetween. The second driving coil may be, but is not limited to, a ring-type coil. When the second driving coil is a ring-type coil, an AC magnetic field may be formed based on the flow of current through the second driving coil. The scan controller 1130 may be formed as a coil in which the selection coil and the second driving coil are combined with each other.

The first AC magnetic field and the second AC magnetic field may have different frequencies. The scan controller 1130 may perform control such that the detection area is scanned along a Lissajous trajectory by adjusting the phase or frequency of the second AC magnetic field. Alternatively, the magnetic field provider 1110 may perform control such that the detection area is scanned along a Lissajous trajectory by adjusting the phase or frequency of the first AC magnetic field. However, the present invention is not limited thereto, and the scan controller 1130 may perform control such that the detection area is scanned in any of various manners. For example, the scan controller 1130 may scan the detection area in a rectangular scan pattern.

Unlike the image scan device 1100 of FIG. 11, the magnetic field provider 1110, the induced signal detector 1120, and the scan controller 1130 may be arranged in different directions. Also, the magnetic field provider 1110, the induced signal detector 1120, or the scan controller 1130 may include additional components. For example, the magnetic field provider 1110, the induced signal detector 1120, or the scan controller 1130 may further include coils arranged to face each other in a third direction (not illustrated) perpendicular to the first direction DR1 and the second direction DR2.

Since the imaging system and the method for operating the imaging system according to embodiments of the present invention do not use a superconductor (liquid helium), an MRI system for a large-sized sample may be configured at relatively low cost.

Since the imaging system and the method for operating the imaging system according to embodiments of the present invention basically require power consumption less than $1/100$ of the power consumption of a conventional MRI coil system, to which power of about several Kw to several tens of Kw must be essentially supplied (e.g. comparison with the amount of power based on the strength of a generated magnetic field: the proposed system having power consumption that is $1/300$ of power consumption of a typical 3 Tesla (3 T) MRI system, that is, 10 mT-class MRI), the present invention can be operated even in an area in which power supply would otherwise be insufficient.

The imaging system and the method for operating the imaging system according to embodiments of the present invention may move Linear Gradient Fields (LGF) from which MR signals can be acquired by utilizing two or more coils for each axis.

The imaging system and the method for operating the imaging system according to embodiments of the present invention may move LGFs in such a way as to apply different currents to two coil systems (solenoid coils or electromagnet coils) mounted for respective axes.

In an embodiment, the problem of fixing additional coordinates generated due to the movement of LGFs may be solved using a function that is based on the amounts of currents to be applied to respective coils and the strengths of the generated LGFs.

In an embodiment, an image may be finally configured by adding the fixed coordinates to pieces of position information acquired for respective K-spaces configuring LGFs.

The magnetic-field-generating coil system, the imaging system having the magnetic-field-generating coil system, and the method for operating the imaging system according to embodiments of the present invention may move LGFs from which MRI/MPI signals can be acquired by utilizing two or more coils for each axis.

The magnetic-field-generating coil system, the imaging system having the magnetic-field-generating coil system, and the method for operating the imaging system according to embodiments of the present invention may move LGFs in such a way as to apply different currents to two coil systems (solenoid coils or electromagnet coils) mounted for each axis.

The magnetic-field-generating coil system, the imaging system having the magnetic-field-generating coil system, and the method for operating the imaging system according to embodiments of the present invention may fix additional coordinates generated by moving LGFs using a transfer function that is based on the amounts of currents to be applied to respective coils and the strengths of the generated LGFs.

The magnetic-field-generating coil system, the imaging system having the magnetic-field-generating coil system, and the method for operating the imaging system according to embodiments of the present invention may finally configure an image by adding the fixed coordinates to pieces of position information acquired for respective K-spaces configuring the LGFs.

Meanwhile, the descriptions of the present invention are only detailed embodiments for practicing the present invention. The present invention may encompass not only detailed and actually available means but also the technical spirit indicating abstract and conceptual ideas that can be utilized as technology in the future.

What is claimed is:

1. A magnetic-field-generating coil system, comprising:
a first coil configured to generate a first magnetic field;
a second coil arranged to face the first coil and configured to generate a second magnetic field;
a first power source configured to supply a first current to the first coil;
a second power source configured to supply a second current to the second coil; and
a current controller configured to control amounts of the first current and the second current so that a Linear Gradient Field (LGF) is generated or moved by the first magnetic field and the second magnetic field,
wherein the magnetic-field-generating coil system is configured to:
sequentially block power to be applied to individual axes in a magnetic field space formed in a three-dimensional (3D) space;
apply and measure a Radio Frequency (RF) pulse for generating a spin echo, using a coil part on any one axis arranged in a first direction perpendicular to any one power-blocked axis; and
acquire a Magnetic Resonance Imaging (MM) signal, using a coil part on a remaining one axis arranged in a second direction perpendicular to the any one power-blocked axis.

2. The magnetic-field-generating coil system of claim 1, wherein each of the first coil and the second coil is implemented as any one of a solenoid coil, an electromagnet coil, a Helmholtz coil, and a Maxwell coil.

3. The magnetic-field-generating coil system of claim 1, wherein each of the first coil and the second coil comprises a coil part for forming a gradient magnetic field for each axis, and a coil part for finely adjusting a magnetic field.

4. The magnetic-field-generating coil system of claim 1, wherein a spatial position of the LGF is determined based on a transfer function having the amounts of the first and second currents and positions of the first and second magnetic fields as variables.

5. A method for operating a Magnetic Resonance Imaging (MRI) system, comprising:
generating multiple Linear Gradient Fields (LGFs) in respective axial directions by controlling coil currents; and
acquiring MRI information or Magnetic Particle Imaging (MPI) information about an object while moving the multiple LGFs by varying the coil currents,
wherein acquiring the MRI information or the MPI information comprises:
blocking power to be applied to each axis in a magnetic field space formed in a three-dimensional (3D) space;
applying a magnetic field using a coil part for applying a RF pulse; and
acquiring an MRI signal using a coil part located in a direction perpendicular to a direction in which the magnetic field is applied.

6. The method of claim 5, wherein a first coil and a second coil arranged to face the first coil are included in each of the axial directions, and independent currents are supplied to the first and second coils, respectively.

7. The method of claim 6, wherein generating the multiple LGFs comprises controlling currents flowing through the first and second coils.

8. The method of claim 6, wherein acquiring the Mill information or the MPI information comprises detecting a Free Induction Delay (FID) signal from the multiple LGFs.

9. The method of claim 6, further comprising generating K-spaces for respective multiple LGFs.

10. The method of claim 9, wherein pieces of relative position information of the respective multiple LGFs are determined based on a transfer function that has amounts of currents flowing through coils and positions of generated magnetic fields as variables.

11. The method of claim 10, further comprising configuring an image of the object by adding the pieces of relative position information to the K-spaces.

12. The method of claim 5, further comprising scanning the object while moving the multiple LGFs.

13. An imaging system, comprising:
an image scan device for acquiring a detection signal corresponding to Magnetic Resonance Imaging (MRI) information or Magnetic Particle Imaging (MPI) information about an object;
a spectrum signal generation device for transforming the detection signal into a detection spectrum signal;
an image recovery device for generating an image signal for the object based on the detection spectrum signal and a system function; and
a display device for displaying the image signal,
wherein the image scan device comprises a coil system configured to:
generate multiple Linear Gradient Fields (LGFs) in respective axial directions by controlling coil currents;
acquire the detection signal for the object while moving the multiple LGFs by varying the coil currents;
sequentially block power to be applied to individual axes in a magnetic field space formed in a three-dimensional (3D) space;
apply and measure a Radio Frequency (RF) pulse for generating a spin echo, using a coil part on any one axis arranged in a first direction perpendicular to any one power-blocked axis; and
acquire an MRI signal, using a coil part on a remaining one axis arranged in a second direction perpendicular to the any one power-blocked axis.

14. The imaging system of claim 13, wherein the coil system comprises:
a first coil configured to generate a first magnetic field;
a second coil arranged to face the first coil and configured to generate a second magnetic field;
a first power source configured to supply a first current to the first coil;
a second power source configured to supply a second current to the second coil; and
a current controller configured to control amounts of the first current and the second current so that an LGF is generated or moved by the first magnetic field and the second magnetic field.

15. The imaging system of claim 14, wherein the detection signal comprises a Free Induction Delay (FID) signal detected from the multiple LGFs.

16. The imaging system of claim 14, wherein the coil system is provided in each of directions of an X axis, a Y axis, and a Z axis, which are orthogonal to each other.

17. The imaging system of claim 14, wherein the image recovery device fixes additional coordinates generated by moving LGFs using a function that is based on amounts of currents to be applied to the first and second coils and strengths of the generated LGFs.

18. The imaging system of claim 17, wherein the image recovery device finally configures an image of the object by adding the fixed coordinates to pieces of position information acquired for respective K-spaces configuring the LGFs.

* * * * *